US011071528B2

(12) United States Patent
Erhardt et al.

(10) Patent No.: US 11,071,528 B2
(45) Date of Patent: Jul. 27, 2021

(54) SPECIMEN FREEZING RATE REGULATOR DEVICE

(71) Applicant: Cool Lab, LLC, Chelmsford, MA (US)

(72) Inventors: Rolf Erhardt, Mill Valley, CA (US); Brian Schryver, Redwood City, CA (US)

(*) Notice: Subject to any disclaimer, the term of this patent is extended or adjusted under 35 U.S.C. 154(b) by 168 days.

(21) Appl. No.: 16/115,277

(22) Filed: Aug. 28, 2018

(65) Prior Publication Data
US 2019/0059862 A1 Feb. 28, 2019

Related U.S. Application Data

(63) Continuation of application No. 12/819,024, filed on Jun. 18, 2010, now abandoned.

(51) Int. Cl.
| A61B 10/00 | (2006.01) |
| B01L 7/00 | (2006.01) |
| B01L 3/00 | (2006.01) |
| A01N 1/02 | (2006.01) |

(52) U.S. Cl.
CPC ........ *A61B 10/0096* (2013.01); *A01N 1/0263* (2013.01); *B01L 7/50* (2013.01); *B01L 3/5082* (2013.01); *Y10T 29/49826* (2015.01)

(58) Field of Classification Search
CPC ............ A61B 10/0096; A61B 10/0045; A01N 1/0263; A01N 1/0268; A01N 1/0273; B01L 7/04; B01L 7/50; B01L 9/06; B01L 3/5082; B65D 81/18; B65D 81/38; B65D 81/3802; B65D 81/3804; B65D 81/3806; B65D 81/3813; B65D 81/3816; B65D 81/3818
See application file for complete search history.

(56) References Cited

U.S. PATENT DOCUMENTS

| 3,072,362 | A | * | 1/1963 | Allen | B65G 51/06 |
| | | | | | 406/188 |
| 3,607,134 | A | * | 9/1971 | McIntyre | B01L 9/06 |
| | | | | | 422/561 |
| 4,030,314 | A | * | 6/1977 | Strehler | F25D 3/10 |
| | | | | | 435/1.3 |
| 4,455,842 | A | * | 6/1984 | Granlund | A01N 1/02 |
| | | | | | 62/64 |
| 4,530,816 | A | * | 7/1985 | Douglas-Hamilton | ...................... |
| | | | | | B01L 3/508 |
| | | | | | 422/1 |
| 4,955,480 | A | * | 9/1990 | Sexton | B65D 81/18 |
| | | | | | 206/438 |
| 5,008,084 | A | * | 4/1991 | Kelley | B01L 9/06 |
| | | | | | 220/592.25 |

(Continued)

FOREIGN PATENT DOCUMENTS

| GB | 647364 A | * | 12/1950 | ........ A47J 41/0044 |
| WO | WO-9101635 A2 | * | 2/1991 | ............. A01N 1/02 |
| WO | WO-2011159934 A2 | * | 12/2011 | ........... A01N 1/0284 |

*Primary Examiner* — Jianying C Atkisson
*Assistant Examiner* — Miguel A Diaz
(74) *Attorney, Agent, or Firm* — David R. Conklin; Kirton McConkie

(57) ABSTRACT

A system and method for concurrently and uniformly removing thermal energy from a specimen sample. A thermal insulating device is provided comprising an insulating material, the device having a plurality of chambers for receiving specimen samples, the device further includes a thermal ballast whereby the rate of thermal energy removal is controlled and influenced by the thermal ballast.

9 Claims, 4 Drawing Sheets

(56) References Cited

U.S. PATENT DOCUMENTS

| | | | | |
|---|---|---|---|---|
| 5,181,394 | A * | 1/1993 | Schea, III | A61J 1/165 62/371 |
| 5,184,721 | A * | 2/1993 | Wengyn | A61L 2/18 206/366 |
| 5,321,955 | A * | 6/1994 | Leonard | B01L 7/04 62/457.9 |
| 5,689,970 | A * | 11/1997 | Chopas | B01L 7/00 62/372 |
| 5,924,302 | A * | 7/1999 | Derifield | B65D 81/3862 62/371 |
| 6,028,293 | A * | 2/2000 | Nagle | A01N 1/02 206/438 |
| 6,044,650 | A * | 4/2000 | Cook | A61J 1/165 62/130 |
| 6,065,617 | A * | 5/2000 | Cohen | B01L 9/06 211/74 |
| 6,209,343 | B1 * | 4/2001 | Owen | A01N 1/02 252/67 |
| 8,151,593 | B2 * | 4/2012 | Henderson | A01N 1/00 62/341 |
| 9,371,169 | B1 * | 6/2016 | Petrucci | B65B 5/08 |
| 9,664,431 | B2 * | 5/2017 | Mullen | B01L 7/04 |
| 2006/0130733 | A1 * | 6/2006 | Linke | G01K 11/12 116/216 |
| 2006/0162652 | A1 * | 7/2006 | Lang | G01N 1/42 118/429 |
| 2009/0019865 | A1 * | 1/2009 | Henderson | A01N 1/00 62/62 |
| 2009/0173472 | A1 * | 7/2009 | Schryver | G05D 23/192 165/47 |
| 2011/0308271 | A1 * | 12/2011 | Schryver | A01N 1/0263 62/465 |
| 2013/0091890 | A1 * | 4/2013 | Schryver | B01L 7/50 62/440 |
| 2013/0263622 | A1 * | 10/2013 | Mullen | B01L 7/04 62/451 |
| 2014/0335614 | A1 * | 11/2014 | Schryver | F25D 31/006 435/374 |
| 2019/0059862 | A1 * | 2/2019 | Erhardt | A01N 1/0263 |
| 2021/0016955 | A1 * | 1/2021 | Morine | B65D 81/3818 |

* cited by examiner

SPECIMEN FREEZING RATE REGULATOR DEVICE

This application is a continuation of application Ser. No. 12/819,024, Jun. 18, 2010, and entitled SPECIMEN FREEZING RATE REGULATOR DEVICE. This application claims priority to and incorporates herein by reference the above-referenced application, in its entirety.

FIELD OF THE INVENTION

This invention relates to devices that will regulate the rate of heat loss from sample or specimen vials contained within, following placement of the assembly into a lower temperature environment, thereby producing the desired temperature reduction profile. In particular, the device is intended to be used with live cell suspensions to provide the appropriate freezing rate for enhanced cell survival following cryogenic storage.

BACKGROUND OF THE INVENTION

Common and accepted methods for long-term storage of tissues and live cells typically involve long-term storage of the sample at a temperature at which molecular activity is significantly reduced. At sufficiently reduced temperatures, the specimens can be stored most likely indefinitely without degradation. The recovery of live cells preserved by this method is dependent upon minimizing injurious ice crystal growth in the intracellular region both during the freezing process and the thawing process. A combination of two methods for reducing intracellular ice crystal growth is typically applied during the freezing process. The first method involves the addition of a cryoprotectant compound to the tissues or cell suspension solution. The cryoprotectant will permeate the cell membrane and serves to inhibit ice crystal nucleation and growth in both the extracellular and intracellular region. The second method involves the time management of the reduction in sample temperature. By regulating the rate of heat loss from the sample, the exclusion of solute salt and buffer components from forming ice crystals in the extracellular region will concentrate the solutes in the remaining liquid phase. The concentrated solutes will impose an osmotic gradient upon the cell membrane that will draw water from the intracellular region. If the freezing of the intracellular solution is coincident with the appropriate level of water content, the size of the crystals resulting from the crystallization of the remaining intracellular water will not be sufficient to cause damage to the cell. If, however, the degree of water removal from the cell is excessive, or if the exposure of the cells to concentrated extracellular solutes is too long in duration, damage to cellular structures will incur, resulting in reduced cell survival upon thawing. Therefore, there is a range of intracellular water content that is appropriate for cell survival during freezing. Ensuring that the intracellular solidification coincides with the correct level of intracellular water content can be accomplished by controlling the temperature reduction rate profile of the sample. While the optimal temperature reduction profile is dependent upon multiple factors such as cell membrane permeability, cell size and concentration of solutes and cyroprotectant components, once the appropriate reduction profile is established for a specific cell type, the survival rate upon thawing can be consistently achieved by applying the same optimal temperature reduction profile to all samples of the given cell type.

Regulation of the temperature reduction profile can be easily achieved through active thermal management by electronic processor regulation of a freezing chamber. Although the regulated freezing chambers are effective in reproducing the desired temperature reduction rate, the cost of the units can be prohibitive. In addition, the requirement for freezing device availability is not uniform in typical laboratory environments, resulting in freezing backlogs until the chambers become available. Effective and appropriate temperature reduction profiles can also be achieved by passive cooling methodologies. A common practice involves wrapping the specimen vials in towels, cardboard, styrene foam or other insulating materials prior to placement in a mechanical freezer, thereby approximating the temperature reduction profile that will result in recovery of live cells. This method, however, provides inconsistent and sometimes inferior survival rates and most importantly post-thaw cell function or such methods can result in an unintentional and undesirable selection of sub-populations of cells. In addition, due to the subjective aspect of the insulation construction and arrangement of cell vials, the freezing profiles obtained by this practice are variable both within and between laboratories.

A carefully engineered device provides a means for producing more consistent temperature reduction profiles through the use of a plastic container in which an inner receptacle is introduced for holding the specimen vials. Between the container inner walls and the receptacle, a volume of isopropyl alcohol is introduced and the unit is sealed with a screw-cap lid. The loaded assembly is then placed into a mechanical freezer compartment to initiate the freezing process. The alcohol surrounding the specimen vials acts as thermal mass of a magnitude such that the rate of heat transfer to the freezer interior produces the desired temperature reduction profile. The method, however, introduces various burdensome problems. The alcohol level must be properly maintained to achieve repeatable freezing profiles. In addition, the alcohol will absorb atmospheric moisture, thereby altering the heat content of the solution, thus introducing a requirement by the manufacturer that the alcohol be changed every five uses. The alcohol change requirement adds a reoccurring cost to the product in the form of the requirement for a supply of fresh alcohol and the cost of proper toxic waste disposal of the expired alcohol. The requirement for alcohol imposes a potential fire hazard during the alcohol exchange phase or in the event of spillage or breakage of the device. The relatively large thermal mass of the assembly also places a burden on the mechanical freezer causing a transient rise in the interior temperature of the freezer. If archival samples are present in the vicinity of the freezing unit, the samples may experience a thermal cycling that can contribute to premature degradation of the samples. The commercially available device also provides for the arrangement of the specimen vials in two concentric circles relative to the cylindrical axis. This arrangement of the vials imposes a variance in the temperature reduction profile for the inner vials as there is a longer path for the sample heat energy to traverse.

Therefore, there is a need for a passive temperature reduction device for freezing live specimen such as tissues, cells, organs, stem cells, blood, biopsies, cord blood, and other bodily fluids such as urine, nasal and spinal fluid that comprises a minimal thermal mass and that does not require solvent or other components which require replacement or refreshment. The passive temperature reduction device will place the samples in an exact geometrically equivalent position with respect to the insulation material between the sample vials and the device exterior creating an identical path for each sample for thermal energy flux, thereby providing identical temperature reduction profiles. The passive temperature reduction device may also comprise a central chamber into which exchangeable materials of selectable density, geometry, and heat capacity may be placed for the purpose of modifying and tuning the temperature reduction profile of the sample vial contents.

SUMMARY OF THE INVENTION

Some aspects of the specimen freezing rate regulation device provide a method for controlling the temperature reduction rate of specimen vial contents. The device typically comprises a base container wherein receptacle cavities will accept the placement of specimen vials, and a cover which forms an upper seal for the specimen receptacle cavities.

Some embodiments of the device provide a specimen freezing rate regulation device comprising a cylindrical container constructed from an insulating foam material wherein a plurality of cylindrical specimen vial receptacle holes have been introduced in a radial pattern with the cylindrical axis of the receptacle holes parallel to and equidistant from the container axis and equidistant to the container exterior surface. An integral thickness of insulation material is present below the specimen container holes. The specimen receiver holes are exposed to the exterior for insertion and recovery of the specimen vials. The device further includes a cover that will engage the base in a manner that seals the specimen receptacle holes and provides an upper layer of insulating material.

In some embodiments, the base contains a central cavity that may contain air space. In other embodiments, the container central cavity may contain a material that will provide a quantity of thermal energy that will influence the rate of thermal energy reduction of the specimen vial contents during the temperature reduction process.

Further, in other embodiments the specimen freezing rate regulation device comprises a container in which the specimen vials are located within a central cavity. In some instances, the vials may be arranged in an array pattern. For example, in some embodiments the specimen freezing rate regulation device comprises a container with walls constructed from an insulating material that surrounds a central cavity, the device further including a base below the central cavity and walls that is constructed from a material that may differ from the wall material. In some embodiments, a specimen vial rack is contained within the central cavity for holding the specimen vials in a consistent position and orientation. Further, in some embodiments the device includes a cover that will close and seal the central cavity that is constructed from a material that may differ from the wall material. Still further, in some embodiments the device includes a thermally conductive layer interposed between the specimen vial rack and the base. In some embodiments, a thermally conductive layer is interposed between the sample vial rack and the cover, which may or may not be an integral feature of the cover.

DETAILED DESCRIPTION OF THE INVENTION

Figure 1:
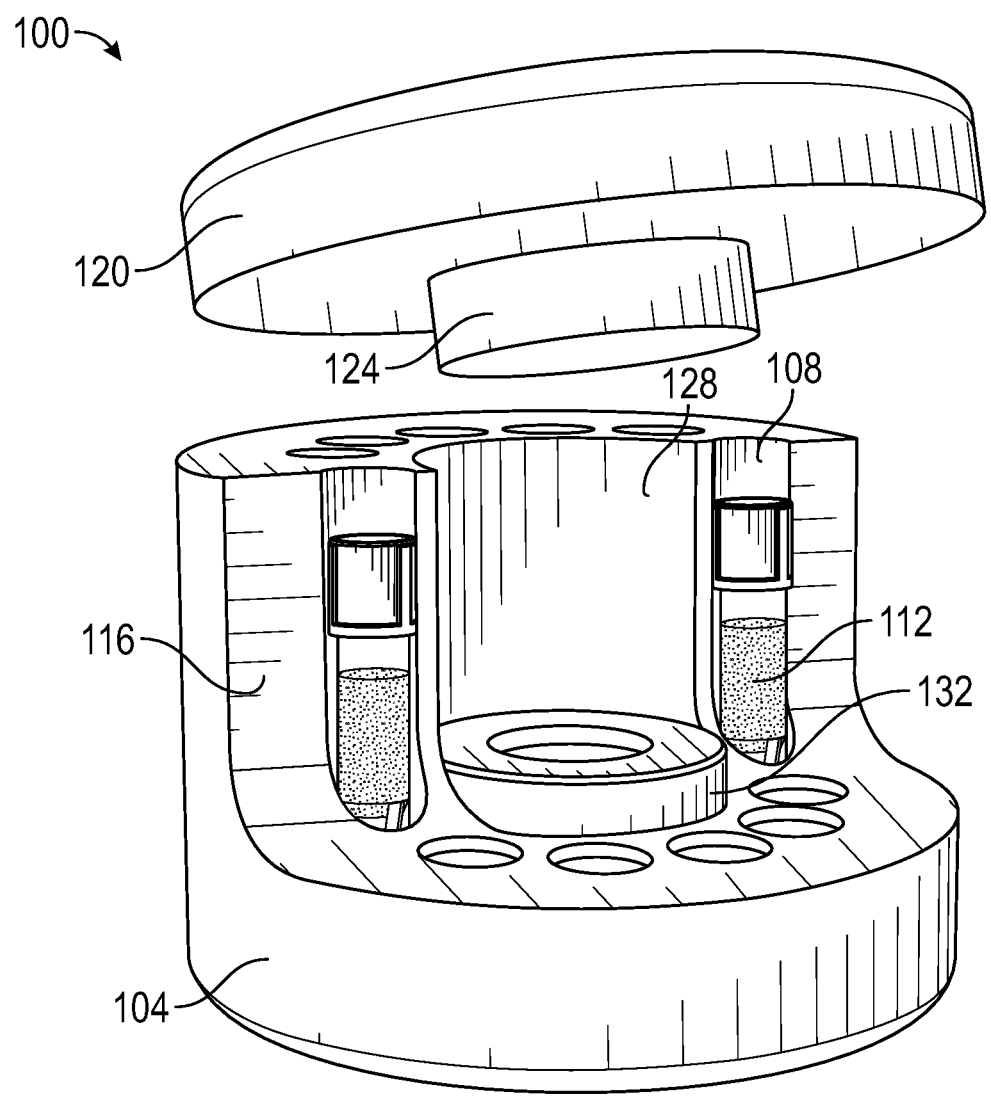
FIG. 1 is a partially cross-section perspective view of a freezing rate regulator device in accordance with a representative embodiment of the present invention.

In biotechnical, clinical, scientific, medical and veterinary laboratories as well as biological and pharmaceutical production and archival facilities, common methods for long term preservation of cellular specimens involve the freezing of the cell specimen followed by storage at cryogenic temperatures. Although extremely rapid freezing or vitrification of a cellular sample is an effective method for freezing and recovering samples intact in a live condition, this method is only effective for samples restricted to a very small volume to minimize the sample heat content. However, for typical archival cell suspensions, much larger sample volumes, typically in the range of 0.5 ml to 1.5 ml, are required. In sample volumes of this magnitude, the slower freezing rate favors the nucleation and growth of ice crystals in both the extracellular and intracellular fluid space. Intracellular ice crystal growth has been associated with damage to cellular organelles and structures resulting in cell death. If, however, the temperature reduction rate can be further reduced, cell survival rates following the freezing process improve.

By regulating the freezing rate, extracellular water will crystallize more gradually and in the process exclude salt and buffer solutes from the ice crystal lattice, concentrating the solutes in the remaining liquid phase. The concentrated solutes create an osmotic gradient across the cell membrane, thereby drawing out intracellular water. When the intracellular water content is reduced to a sufficient level, the remaining intracellular contents can solidify without the risk of the formation of extensive ice crystal structures that will fatally damage cellular organelles and structures. Alternatively, if the freezing rate is too slow, excessive concentration of solutes in the extracellular liquid phase can damage cell surface components again imposing a reduction is cell survival.

While the freezing rate which coincides with optimal percentage of surviving cells will vary from cell type to cell type, once the appropriate freezing rate for a particular cell type has been established, a simple duplication of the same temperature reduction profile for subsequent freezing processes will result in comparable survival rates. Therefore, devices which can provide reliable and consistent freezing rate profiles for specimen vials are of great value in that such devices allow the operator to cryogenically archive cell specimens with confidence that the cells will be recovered alive upon thawing.

Control rate freezers in which the temperature reduction profile is actively managed under the control of a microprocessor provide a very effective means of ensuring fidelity to the desired profile. The large cost of actively regulated freezing units limits the availability of the devices. Passive temperature reduction profile control devices that influence the rate of heat loss, and therefore regulate the temperature reduction profile of the cell samples, can provide a cost effective alternative to actively regulated freezing units. Passive freezing rate regulation devices, through a combination of construction material selection, design geometry, sample vial positioning, and material heat content, can produce a close approximation of the ideal freezing rate profile for a given cell type when the assembly is introduced into a cold environment such as is typically found in the interior of mechanical deep freezers.

In numerous laboratories, a common method for producing an effective freezing rate profile in specimen vials involves simply enclosing the vials in available insulating material such as styrene foam, paper towels, cardboard and paper tissue. Although cell samples frozen by these methods can contain an acceptable percentage of live cells upon thawing, the non-ideal freezing conditions can impose stresses upon the cell populations which will unintentionally select for the more stress-resistant subpopulations of the cells, leading to undesirable or misleading outcomes when the cells are used in downstream applications.

Commercially available passive freezing rate regulation devices provide a much more consistent sample temperature reduction profile, as the device geometry and heat capacity are more consistent and reproducible. Some embodiments of available passive devices provide a receptacle for the sample vials with the receptacle partially submerged in a tank of isopropanol contained in a plastic housing. A screw lid seals the assembly before the freezing cycle is initiated by placing the device in a mechanical deep freezer. Although effective in producing an acceptable freezing profile, devices of this construction method have undesirable aspects. The volume of the isopropanol contained within the device must be monitored and adjusted to the proper level. In addition, the isopropanol will absorb atmospheric moisture, thereby altering the heat capacity of the solution and changing the temperature reduction profile of the device. As a consequence, the manufacturer recommends that the isopropanol be exchanged for fresh 100% isopropanol every 5 uses of the device. The incurrent cost of the replacement solvent in addition to the expense of proper disposal of the solvent into accepted toxic waste streams supports the desirability of a solvent-free alternative. The large thermal mass of the isopropanol in relation to the lesser thermal mass of the samples also places a burden upon the cooling mechanism of the freezer into which it is placed. As the heat content of the device assembly must be dissipated through the local freezer environment, archival samples stored in the vicinity will experience a rise in temperature. Transient and cyclic changes in temperature are a known factor contributing to the degradation of biological samples.

Devices and apparatuses of the present invention provide similar or identical temperature reduction profiles to those obtained by commercially available isopropanol-based passive temperature regulation devices. Devices of the present invention comprise a cylindrical container into which a radial arrangement of receptacle holes are present for the purpose of receiving sample tube vials. The container houses a central, coaxial chamber and is closed with an insulation cover that seals the tube receptacles and engages and seals the central chamber. Sample vials can be inserted and enclosed by engaging the cover pedestal in the central chamber cavity thereby effectively sealing the vials in the individual chambers. When placed into an environment with a lower temperature, such as a deep freezer, the insulation surrounding the vials will provide for a controlled reduction in temperature of the sample vials. The rate of the temperature reduction can be adjusted by increasing or decreasing the thickness of the insulation layer surrounding the samples. Devices of the invention may also provide for a secondary means of controlling the temperature through the inclusion of a thermal ballast mass placed in the central, coaxial chamber of the container. During the freezing process, the heat energy content of the thermal ballast mass will be conducted partially through the samples contained in the surrounding receptacle chambers, thereby altering the temperature reduction profile of the vial contents.

The present invention will be described with regard to the accompanying drawings which assist in illustrating various features of the invention.

As used herein, the terms "sample vials" and "specimen vials" are used interchangeably to refer to various commercially available tubes with enclosure caps, typically constructed from plastic materials, that are intended for containing primarily, but not exclusively, liquid contents, and which are intended for storage of the contents in a range of temperatures extending to cryogenic temperatures.

Some of the features of the invention are generally illustrated in FIG. 1 which is provided for the purpose of illustrating the practice of the invention and which does not constitute limitations of the scope thereof.

Referring to FIG. 1, the specimen freezing rate regulator device 100 comprises a container or enclosure 104 into which a series of receptacle holes or specimen containment chambers 108 have been introduced for the purpose of housing the sample vials 112. In some embodiments, enclosure 104 comprises a cylindrical insulation base. The array of receptacle holes is arranged in a radial pattern in relation to the cylindrical axis of the container. Surrounding the receptacle hole array is a uniform layer of insulation material 116. A removable cover 120 seals the upper end of the receptacles and engages the container by means of a central protrusion 124 that extends into the central cavity of the container 128 and mates with a friction fit at the wall of the cavity. In some embodiments, a central mass thermal ballast 132 is provided to modify and adjust the temperature reduction profile of the tubes during the freezing process. In some embodiments, the thermal ballast is coaxially positioned within ballast chamber 128 such that thermal ballast 132 is thermally coupled to at least one of the specimen chamber 108, the enclosure 104, the specimen sample 112, the ballast chamber 128, and the cover 120.

Figure 2:
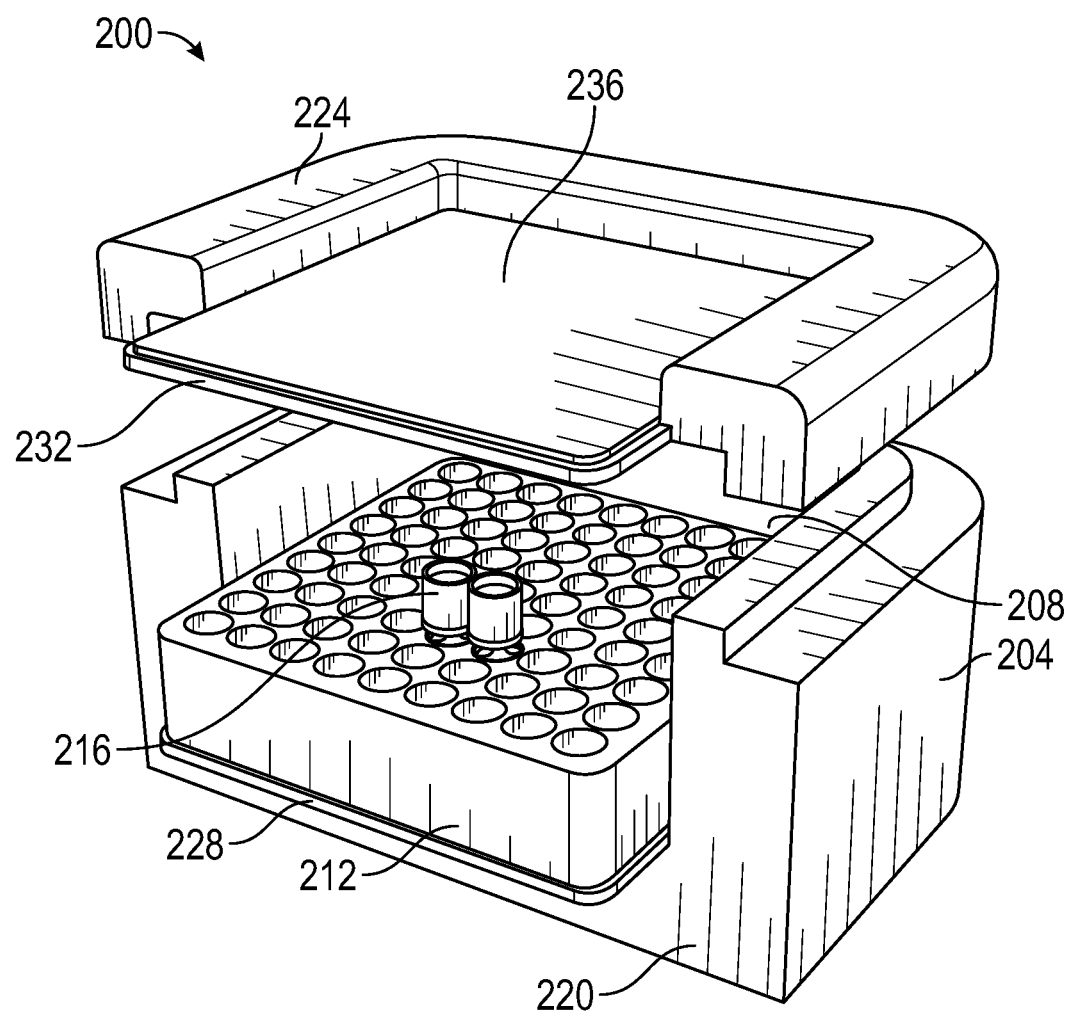
FIG. 2 is a partially cross-section perspective view of a freezing rate regulator device in accordance with a representative embodiment of the present invention.

Some of the features of the second embodiment of the invention are generally illustrated in FIG. 2 which is provided for the purpose of illustrating the practice of the invention and which do not constitute limitations of the scope thereof.

Referring now to FIG. 2, the specimen freezing rate regulator device 200 comprises four lateral walls constructed from an insulating material 204 which surrounds and contains a central cavity 208. The central cavity receives a specimen tube rack 212 that positions and retains an array of specimen sample vials 216. The lateral insulation walls are bordered on the underside by a thickness of a material 220 which may be identical to the material from which the lateral walls are constructed or may be constructed from a different material. The upper side of the lateral walls are bordered by a partial cover 224 which acts as a removable continuation of the lateral walls and which may be identical to the material from which the lateral walls are constructed or may be constructed from a different material.

In some embodiments, partial cover 224 houses an upper thermoconductive layer 232. Directly under the specimen tube rack 212 is placed a layer of thermoconductive material 228 which serves to uniformly distribute the thermal energy present in the central cavity 208. Directly above the specimen tube rack 212 is placed a layer of thermoconductive material 232 that acts to radiate the heat contained within the central cavity to the exterior. In some embodiments, a layer of insulation 236 is provided to cover upper thermoconductive layer 232 and modify the rate at which thermal energy is conducted from the thermoconductive material 232 to the surrounding environment. Further, in some embodiments the thermoconductive materials 228 and 232 are interposedly positioned between the specimen chamber and at least one of the enclosure and the cover, such that at least one of the thermoconductive materials are in thermal contact with at least one of the insulation materials 116, 220, 224 and 236.

In some embodiments, insulation materials 116, 220, 224 and 236 are constructed as both integral structural features and as insulating materials to their respective devices 100 and 200. In other embodiments, insulation materials 116, 220, 224 and 236 comprise a material such as, but not limited to, uniform density cross-linked closed-cell polyethylene foam rubber, uniform density polystyrene foam, closed-cell polyurethane foam materials, and combinations thereof. In some embodiments, an open-cell insulation material is utilized. In other embodiments, the insulating material comprises at least one of a solid foam material and a synthetic material. Further, in some embodiments, device 100 and 200 further comprises an exterior insulating material to reduce heat transfer to and from the operator during physical contact. Still further, in some embodiments an exterior insulating material is selected to prevent, reduce, remove, and/or absorbed moisture, such as condensation, from an external surface of the device.

In some embodiments, central ballast material 132 is constructed from a range of materials including, but not limited to, metals, metal alloys, ceramics, sealed liquid containers, plastics, glass, cast materials such as waxes, and synthetic materials such as silicone. In some embodiments, thermoconductive layers 228 and 232 comprise materials such as, but not limited to, metals and metal alloys, ceramics, plastics and plastic compounds. Further, in some embodiments specimen tube rack 212 comprises materials such as, but not limited to, polyethylene open cell foam, polyethylene closed cell foam, plastic or synthetic foam materials such as urethane foam, cardboard, metal, metal alloys, and solid or mesh plastics or synthetic materials.

EXAMPLES

Experiment 1: Repeatability of Specimen Freezing Cycle

Figure 3:
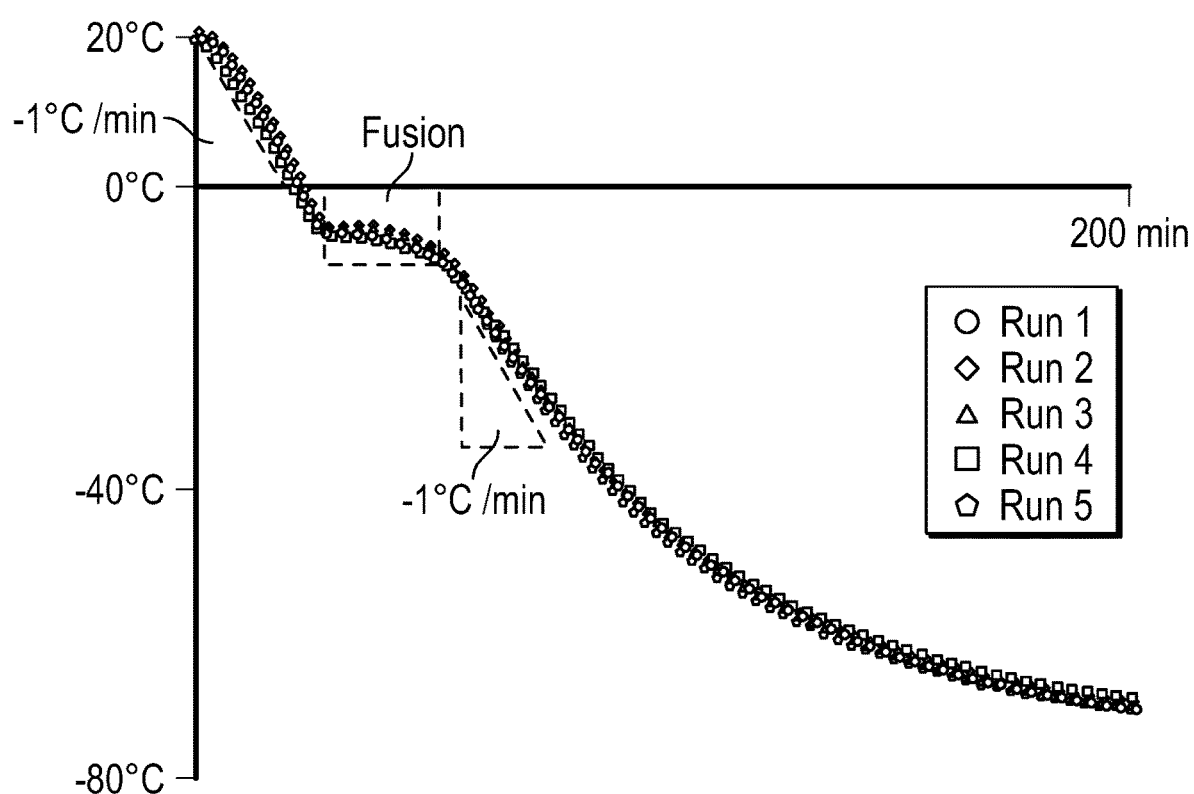
FIG. 3 is graphic representation of five consecutive specimen freezing cycles conducted using a freezing rate regulator device in accordance with a representative embodiment of the present invention, the figure illustrating the consistency of the specimen temperature reduction profiles produced by the device.

With reference to FIG. 3, the results from an experiment are shown. This experiment was conducted using a prototype device 100 as shown in FIG. 1. The device 100 was loaded with 12 specimen vials containing 1 ml of cryoprotectant solution each. The device 100 was then closed by replacing the cover, and the device and cover were placed in a −80° C. freezer compartment. The cryoprotectant load of one vial was monitored using a thermocouple probe introduced through the cover of the device and through the screw-cap lid of the specimen vial. The temperature of the cryoprotectant solution was recorded using an electronic data recorder that collected sample data at 10 second intervals. Following a four hour interval, the assembly was removed from the freezer disassembled and the device and sample vials re-equilibrated to 20° C. The sample vials were re-loaded and the freezing cycle described was repeated a total of 5 times. The combined graphic plots of the temperature reduction profiles of the sample tube contents reveals that very consistent and reliable profiles are produced when the device is used under the same physical conditions.

Experiment 2: Specimen Freezing Rate Regulator with Central Ballast Mass

Figure 4:
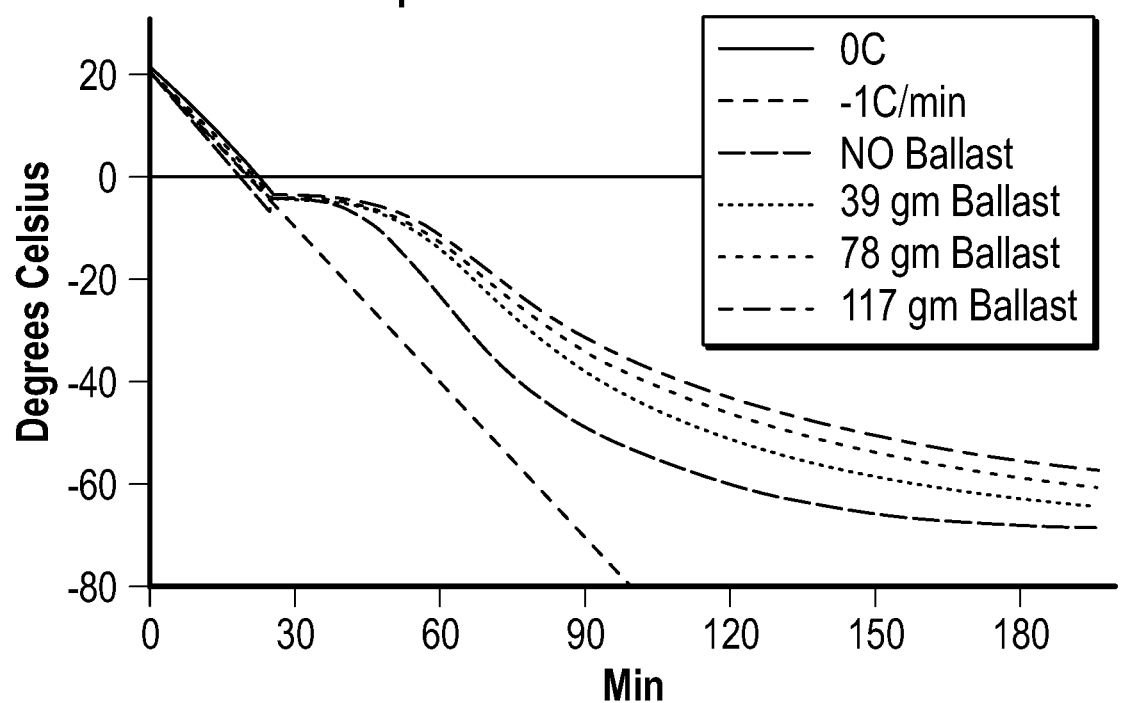
FIG. 4 is a graphic representation of temperature reduction profile data as a function of central thermal ballast mass, obtained with a freezing rate regulation device in accordance with a representative embodiment of the present invention.

With reference to FIG. 4, the results from an experiment are shown. This experiment was conducted using a prototype device 100 with and without a ballast 132, as shown in FIG. 1. The device 100 was loaded with 12 specimen vials containing 1 ml of cryoprotectant solution each, then closed by replacing the cover after which the assembly was placed in a −80° C. freezer compartment. The cryoprotectant load of one vial was monitored using a thermocouple probe introduced through the cover of the device and through the screw-cap lid of the specimen vial. The temperature of the cryoprotect solution was recorded using an electronic data recorder that collected sample data at 10 second intervals. Following a four hour interval, the assembly was removed from the freezer disassembled and the device and sample vials re-equilbrated to 20° C.

Four separate freezing cycles are shown in which the central cavity of the device contained no additional thermal ballast mass, or contained a ballast mass of 39 gm, 78 gm, or 117 gm. Shifts in the temperature reduction rate plot were observed by changing the thermal mass present in the central cavity, as shown in FIG. 4. Accordingly, the present experiment demonstrates the effectiveness of the temperature profile modification feature of the invention.

The device of the present invention can be used to properly prepare cell suspension samples for cryogenic storage by providing the appropriate temperature reduction rate profile during the freezing process. For example, the device can be used to freeze any cell suspension in which the optimal temperature reduction rate for the specific cell population coincides with the freezing rate specification to which the specimen freezing rate regulator device has been constructed to provide.

Typically, the freezing rate regulator device of the present invention would be equilibrated to the temperature at which the loaded specimen vials are maintained prior to the initiation of the freezing process. The cover of the device would be removed and the specimen vials loaded into the receptacle holes. The cover would be replaced and the device assembly would be placed into a −80° C. freezer and enclosed undisturbed for a period of greater than 4 hours. The device assembly would then be recovered, the cover would be removed and the container inverted to recover the frozen vials. The vials would be immediately transferred to an archival cryogenic storage container system or cooled by material phase change, such as by being placed onto a layer of dry ice or into a container of liquid nitrogen, for more extended transfer time intervals prior to archival storage. The freezing rate regulator device would then be allowed to equilibrate to the starting temperature once again prior to initiation of a subsequent freezing cycle.

In some embodiments, the freezing rate regulator device is use to preserve a wide variety of cultured mammalian and non-mammalian cells including, but not limited to, primary cell cultures, established immortalized cell lines, stem cell lines, and isolated blood cells.

In some embodiments, a thermal regulating device is provided or manufactured by first providing a thermally insulated specimen chamber into which a specimen sample may be loaded. The specimen chamber is then encased within an insulation base, the insulation base being comprised of an insulating material. The thermal regulating device is further manufactured by providing a cover for the insulation base, the cover being removably coupled to the insulation base and forming a thermal seal between the specimen chamber and the cover. In some embodiments, a thermal ballast is further provided such that the thermal ballast is in thermal contact with at least one of the insulation base, the specimen chamber, the specimen sample, and the cover.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps are disclosed herein, and without intending to publicly dedicate any patentable subject matter.

What is claimed is:

1. A method for freezing a specimen sample, said method comprising:

acclimating to a first temperature a specimen freezing rate regulator device, comprising:

a container composed of an insulating material and having a sidewall, a bottom, and a central cavity, the container comprising a plurality of specimen containment chambers formed in the sidewall and positioned between the central cavity and an outer surface of the container, each specimen containment chamber and the central cavity having an opening, wherein a position of each specimen containment chamber is an exact geometric equivalent position with respect to the insulation material between each specimen containment chamber, the bottom of the container, and the outer surface of the container; and a cover composed of the insulating material that is adapted to removably couple to the opening of the central cavity and adapted to cover the openings of the specimen containment chambers and the central cavity when coupled to the opening of the central cavity;

acclimating to the first temperature a thermal ballast;
   acclimating to the first temperature a sample tube vial;
   acclimating to the first temperature a specimen sample;
   assembling the acclimated specimen freezing rate regulator device by:
   disposing the acclimated specimen sample into the sample tube vial;
   inserting the acclimated sample tube vial into one of the plurality of specimen containment chambers of the acclimated specimen freezing rate regulator device;
   inserting the acclimated thermal ballast into the central cavity; and
   securing the acclimated cover to the acclimated container thereby enclosing the acclimated thermal ballast, sample tube vial, and specimen sample therein; and placing the acclimated assembled specimen freezing rate regulator device into an environment having a second temperature that is less than the first temperature.

2. The method of claim 1, further comprising a step for controlling a reduction of the acclimated temperature of the specimen sample by conducting heat energy from the thermal ballast to the specimen sample through the central cavity and specimen containment chambers.

3. The method of claim 1, further comprising a step for reducing the acclimated temperature of the specimen sample at a freezing rate of $-1°$ C./min.

4. The method of claim 1, wherein the plurality of specimen containment chambers consist of a single row arranged in a radial pattern in relation to the central cavity and maintained at an equal distance from the central cavity by a uniform layer of the insulating material, the plurality of specimen containment chambers being maintained at an equal distance from the outer surface of the container by a uniform layer of insulating material, a uniform layer of insulating material further interposed between each adjacent specimen containment chamber to maintain an equal distance between each specimen containment chamber, and a uniform layer of insulating material interposed between the bottom of the container and a bottom of each specimen containment chamber.

5. The method of claim 1, wherein the openings of each specimen containment chamber and the central cavity are in an identical plane.

6. The method of claim 1, wherein the container is a monolithic structure.

7. The method of claim 1, wherein the exact geometric equivalent position of each specimen containment chamber provides an identical temperature reduction profile for a specimen sample inserted therein.

8. The method of claim 1, wherein the thermal ballast comprises a metal or a metal alloy excluding sealed liquid containers.

9. The method of claim 1, further comprising a step for sealing the acclimated sample tube vial and specimen sample within one of the plurality of specimen containment chambers by securing the acclimated cover to the acclimated container.

* * * * *